United States Patent [19]

Voronkov et al.

[11] 4,251,666

[45] Feb. 17, 1981

[54] METHOD OF PRODUCING THIOPHENE

[76] Inventors: Mikhail G. Voronkov, ulitsa Lermontova, 315, kv. 32; Boris A. Trofimov, ulitsa Lermontova, 321$^a$, kv. 32, both of Irkutsk; Vasily V. Krjuchkov, prospekt Lenina, 65, kv. 92, Kemerovo; Svetlana V. Amosova, ulitsa Dekabrskikh sobyty, 105"b", kv, 43, Irkutsk; Jury M. Skvortsov, ulitsa Lermontova, 315, kv. 14, Irkutsk; Anatoly N. Volkov, ulitsa Lermontova, 321$^a$, kv. 25, Irkutsk; Anastasia G. Malkina, ulitsa Lermontova, 281, kv. 51, Irkutsk; Roman Y. Mushy, ulitsa Lisichanskaya, 45, kv. 15, Severodonetsk, all of U.S.S.R.

[21] Appl. No.: 97,444

[22] Filed: Nov. 26, 1979

Related U.S. Application Data

[63] Continuation of Ser. No. 897,268, Apr. 18, 1978, abandoned.

[51] Int. Cl.$^3$ .......................................... C07D 333/12
[52] U.S. Cl. .................................................... 549/29
[58] Field of Search ......................................... 549/29

[56] References Cited

FOREIGN PATENT DOCUMENTS 1202796 10/1965 Fed. Rep. of Germany ............. 549/29

OTHER PUBLICATIONS

Schulte et al., "Thiophene aus Alinen, I", Chem. Ber. 95, BP. 1943–1954 (1962).

*Primary Examiner*—A. Siegel
*Attorney, Agent, or Firm*—Fleit & Jacobson

[57] ABSTRACT

A method of producing thiophene, residing in interacting diacetylene with sodium sulphide in a mixture of an aprotic polar solvent with water, in a weight ratio 50–90:50–10, respectively, or in water at a temperature of 20°–100° C. The method ensures quantitative yield of thiophene with a high degree of purity (more than 99.0% by gas-liquid chromatography). The method is technologically simple and does not require complicated equipment.

9 Claims, No Drawings

METHOD OF PRODUCING THIOPHENE

This is a continuation of application Ser. No. 897,268 filed Apr. 18, 1978, now abandoned.

FIELD OF APPLICATION OF THE INVENTION

The present invention relates to methods of producing thiophene. Thiophene and its homologs are widely used for the synthesis of higher hydrocarbons of a prescribed structure, alcohols, acids, esters, additives to fuels and oils, polymers with valuable dielectric properties, fluorescent materials, and chemicals for agriculture.

BACKGROUND OF THE INVENTION

Known in the art are methods of producing thiophene and its derivatives by interacting various organic compounds, such as crotonic acid, pyrrol, furan, ethylene, propylene, butylene, butane, acetylene, etc., with sulphur-containing compounds, for example, hydrogen sulphide.

But it is difficult to accomplish the majority of the known methods even under laboratory conditions. This is associated, mainly, either with a high cost of the initial components or with technological difficulties which arise in the process and especially when isolating thiophene from the reaction mixture.

Also known in the art is a method of producing thiophene by isolation thereof from a benzene fraction of coal-tar chemicals. This method is technologically complicated.

Likewise known in the art is a method of producing thiophene by interacting diacetylene with hydrogen sulphide in an aliphatic alcohol or acetone in the presence of sodium hydroxide (pH=9–10) at a temperature of 20°–80° C.

Also known in the art is a method of producing thiophene by interacting diacetylene with sodium sulphide in the form of a saturated aqueous solution in an aliphatic alcohol or in acetone.

The above methods of producing thiophene from diacetylene are disadvantageous in that the yield of the final product is low (to 20% of theory). Therefore, the known methods have found application neither in industry nor in preparative chemistry. In addition the use of low-boiling aliphatic alcohols as a solvent makes the separation of thiophene difficult.

BRIEF DESCRIPTION OF THE INVENTION

It is an object of this invention to provide a technologically simple method of producing thiophene, which will be based on the available stock material and ensure high yield of a high-quality end product;

In accordance with this and other objects of the invention a method is proposed of producing thiophene by interacting diacetylene with sodium sulphide in a solvent at a temperature of 20°–100° C. According to the invention, use is made of a mixture of an aprotic polar solvent with water in a weight ratio of 50–90:50–10, respectively, or water alone, as a solvent.

Dimethylsulphoxide, hexamethylphosphortriamide, or N-methylpyrrolidone are preferred for use as the aprotic polar solvent.

The reaction can be conducted with a catalyst or without a catalyst (the yield of thiophene in this case does not exceed 54% of theory).

As a catalyst use can be made of an alkali (NaOH or KOH) with a molar ratio between the alkali and sodium sulphide of from 0.1:1 to 2:1. The use of the catalyst makes it possible to increase the yield of the end product, under the conditions of the proposed method, up to 94% of theory. It should be noted that commercial alkali will be needed only at the beginning of the process, whereas in the subsequent run of the process use can be made of the alkali liberated during the reaction.

To intensify the process, it is recommendable to interact diacetylene with sodium sulphide at a temperature of 40°–70° C.

Thus, under the conditions of the proposed method, it becomes possible to obtain thiophene in a quantitative yield. Thiophene distilled off under from the reaction mixture is characterized, even without additional purification, by a high degree of purity (more than 99.0% as determined by GLC). The method is technologically simple and based on readily available stock material.

DETAILED DESCRIPTION OF THE INVENTION

The proposed method of producing thiophene is accomplished in the following way.

A solvent, sodium sulphide, and, if necessary, alkali are charged into a reactor fitted with a stirrer and a reflux condenser. The resultant mixture is heated up to a preset temperature (20°–100° C.) and diacetylene in a nitrogen flow is passed through the mixture. On completion of the reaction, thiophene is separated from the reaction mixture.

For instance, when use is made of a mixture containing 90 wt.% of an aprotic polar solvent and 10 wt.% of water, as a solvent, thiophene can be separated by vacuum distillation; if water alone is used as a solvent, thiophene is separated from an aqueous layer.

For the synthesis of thiophene by the proposed method it is not necessary to use pure diacetylene. Diacetylene containing gases of acetylene production can equally be used since other components of these gases (for example, methylene, etc.) are inert under the above-cited conditions.

For a better understanding of the present invention specific examples thereof are given below by way of illustration.

EXAMPLE 1

65 ml of dimethylsulphoxide (DMSO), 20 g (0.083 M) of $Na_2S.9H_2O$ and 4.5 g (0.08 M) of KOH are put into a three-necked flask fitted with a stirrer and a reflux condenser. 1.9 g (0.038 M) of diacetylene in a nitrogen flow are passed through the DMSO at 55° C. for 75 min., and 3.0 g (93.9% of theory) of thiophene are separated from the reaction mixture by vacuum distillation. The degree of purity is 99.9%, boiling point, 83.5° C./720 mm Hg; $n_d^{20}$, 1.5285.

Found, %: C,57.2; H,4.6; S,38.18. $C_4H_4S$.

Calculated, %: C,57.10; H,4.79; S,38.11.

The structure of the product is confirmed by IR and PMR spectra.

EXAMPLE 2

65 ml of DMSO and 34.6 g (0.14 M) of $Na_2S.9H_2O$ are put into a flask fitted with a stirrer and a reflux condenser. 3.6 g (0.072 M) of diacetylene in a weak nitrogen flow are passed through the DMSO at 100° C. for 75 minutes, and 2.4 g (40% of theory) of 99.9% pure thiophene are separated from the reaction mixture by vacuum distillation.

EXAMPLE 3

65 ml of DMSO and 26 g (0.108 M) of $Na_2S.9H_2O$ are put into a flask fitted with a sitrrer and a reflux condenser. 2.7 g (0.054 M) of diacetylene in a weak nitrogen flow are passed under stirring through the DMSO at 20° C. for 90 minutes, and 2.0 g (44.1% of theory) of 99.9% pure thiophene are separated from the reaction mixture by vacuum distillation.

EXAMPLE 4

65 ml of DMSO and 14.8 g (0.061 M) of $Na_2S.9H_2O$ are put into a flask fitted with a stirrer and a reflux condenser. 6 g (0.12 M) of diacetylene in a weak nitrogen flow are passed through the DMSO at 70° C. for 90 minutes, and 5.5 g (54.6% of theory) of 99.9% pure thiophene are separated from the reaction mixture by vacuum distillation.

EXAMPLE 5

65 ml of DMSO, 15 g (0.1 M) of $Na_2S.4H_2O$, and 5.6 g (0.1 M) of KOH are charged into a flask fitted with a stirrer and a reflux condenser. 2.6 g (0.052 M) of diacetylene in a weak nitrogen flow are passed through under intensive stirring at 50° C. for 80 min. 4 g (91% of theory) of 99.8% pure thiophene are obtained.

EXAMPLE 6

65 ml of DMSO, 20 g (0.083 M) of $Na_2S.9H_2O$, and 0.45 g (0.008 M) of KOH are put into a flask fitted with a stirrer and condenser. 3 g (0.06 M) of diacetylene in a weak nitrogen flow are passed through under stirring at 45° C. for 90 minutes. 2 g (40% of theory) of 99.8% pure thiophene are obtained.

EXAMPLE 7

65 ml of DMSO, 18.6 g (0.1 M) of $Na_2S.6H_2O$, and 2.3 g (0.05 M) of KOH are put into a flask fitted with a stirrer and a reflux condenser. 2.9 g (0.06 M) of diacetylene in a weak nitrogen flow are passed through under intensive stirring at 80° C. for 90 min. 3.2 g (60% of theory) of 99.0% thiophene are obtained.

EXAMPLE 8

65 ml of DMSO, 16.2 g (0.9 M) of $H_2O$, 7.8 g (0.1 M) of $Na_2S$, and 5.6 g (0.1 M) of KOH are put into a flask with a stirrer and a reflux condenser. 2.5 g (0.05 M) of diacetylene in a weak nitrogen flow are passed through under intensive stirring at 60° C. for 90 minutes. 3.8 g (92% of theory) of 99.8% pure thiophene are separated from the reaction mixture.

EXAMPLE 9

65 ml of DMSO, 24 g (0.1 M) of $Na_2S.9H_2O$, and 4 g (0.1 M) of NaOH are put into a flask fitted with a stirrer and a reflux condenser. 5 g (0.1 M) of diacetylene in a weak nitrogen flow are passed through under intensive stirring at 30° C. for 185 min. After that 4.2 g (50% of theory) of 99.2% pure thiophene are separated from the reaction mixture.

EXAMPLE 10

100 ml of N-methylpyrrolidone, 24 g (0.1 M) of $Na_2S.9H_2O$, and 5.6 g (0.1 M) of KOH are charged into a flask fitted with stirrer and a reflux condenser. 4 g (0.08 M) of diacetylene are passed through in a weak nitrogen flow for 165 min. at 55° C. 3.7 g (55% of theory) of 98.1% pure thiophene are separated from the reaction mixture by vacuum distillation.

EXAMPLE 11

200 ml of hexamethylphosphortriamide, 24 g (0.1 M) of $Na_2S.9H_2O$, and 5.6 g (0.1 M) of KOH are put into a flask fitted with a stirrer and a reflx condenser. 2.1 g (0.042 M) of diacetylene in a weak nitrogen flow are passed through under intensive stirring for 110 min. at 55° C. 2.33 g (67% of theory) of 98.0% pure thiophene are separated from the reaction mixture by vacuum distillation.

EXAMPLE 12

100 ml of water, 36.4 g (0.15 M) of $Na_2S.9H_2O$, and 20.2 g (0.36 M) of KOH are put into a flask with a stirrer and condenser. 2.7 g (0.054 M) of diacetylene are passed through under intensive stirring in a weak nitrogen flow for 105 min. at 70° C. 2.36 g (52.5% of theory) of thiophene 98.5% pure are separated from the reaction mixture.

EXAMPLE 13

80 ml of water, 72 g (0.3 M) of $Na_2S.9H_2O$, and 16.8 g (0.3 M) of KOH are charged into a flask fitted with a stirrer and a reflux condenser. 2.6 g (0.052 M) of diacetylene in a weak nitrogen flow are passed through under intensive stirring at 70° C. for 90 min. 2.1 g (48.5% of theory) of 99.0% pure thiophene are separated from the reaction mixture.

EXAMPLE 14

65 ml of DMSO, 48.8 ml of $H_2O$, 24 g (0.1 M) of $Na_2S.9H_2O$, and 11.2 g (0.2 M) of KOH are put into a flask fitted with a stirrer and a reflux condenser. 2.9 g (0.058 M) of diacetylene in a weak nitrogen flow are passed through under intensive stirring at 55° C. for 205 minutes. 1.74 g (33.8% of theory) of 98.0% pure thiophene are obtained by vacuum distillation of the reaction mixture and subsequent separation of thiophene from an aqueous layer.

What is claimed is:

1. A method of producing thiophene comprising the step of reacting diacetylene with sodium sulfide in either water or a mixture of from about 50–90 parts by weight of a polar aprotic solvent selected from the group consisting of dimethylsulphoxide, hexamethylphosphortriamide and N-methylpyrrolidone and from about 50–10 parts by weight of water at a temperature of from about 20°–100° C., the water being either free water or water of hydration.

2. The method of claim 1 wherein the solvent is a mixture of the polar aprotic solvent and water.

3. The method of claim 1 wherein a catalyst selected from the group consisting of sodium hydroxide and potassium hydroxide is present in a catalyst to sodium sulfide molar ratio of 0.1–2:1.

4. The method of claim 1 wherein the reaction is conducted at a temperature of from 40° to 70° C.

5. The method of claim 2 wherein the polar aprotic solvent is dimethylsulphoxide.

6. The method of claim 5 wherein about 0.038 mole of diacetylene is reacted with about 0.083 mole of sodium sulfide in the presence of about 0.08 mole of potassium hydroxide catalyst and at a temperature of about 55° C.

7. The method of claim 5 wherein about 0.052 mole of diacetylene is reacted with about 0.1 mole of sodium sulfide in the presence of about 0.1 mole of potassium hydroxide catalyst at a temperature of about 50° C.

8. The method of claim 5 wherein about 0.05 mole of diacetylene is reacted with about 0.1 mole of sodium sulfide in the presence of about 0.1 mole of potassium hydroxide catalyst at a temperature of about 60° C.

9. The method of claim 5 wherein from about 0.038 to about 0.052 mole of diacetylene is reacted with from about 0.083 to about 0.1 mole of sodium sulfide in the presence of from about 0.08 to about 0.1 mole of potassium hydroxide catalyst and at a temperature of from about 50° to about 60° C.

* * * * *